(12) United States Patent
Kashkoush et al.

(10) Patent No.: US 11,657,488 B2
(45) Date of Patent: May 23, 2023

(54) METHODS AND SYSTEMS RELATED TO MUSHROOM RIPENESS DETERMINATION (71) Applicants: Vineland Research and Innovation Centre, Vineland Station (CA); NATIONAL OPTICS INSTITUTE, Quebec (CA)

(72) Inventors: Mohamed Kashkoush, Hannon (CA); Gideon Avigad, London (CA); Patrick Dallaire, Quebec (CA)

( * ) Notice: Subject to any disclaimer, the term of this patent is extended or adjusted under 35 U.S.C. 154(b) by 232 days.

(21) Appl. No.: 16/772,329

(22) PCT Filed: Dec. 12, 2018

(86) PCT No.: PCT/CA2018/051580
§ 371 (c)(1),
(2) Date: Jun. 12, 2020

(87) PCT Pub. No.: WO2019/113691
PCT Pub. Date: Jun. 20, 2019

(65) Prior Publication Data
US 2021/0082104 A1    Mar. 18, 2021

Related U.S. Application Data (60) Provisional application No. 62/599,225, filed on Dec. 15, 2017.

(51) Int. Cl.
*G06T 7/00* (2017.01)
*A01G 18/00* (2018.01)
*G01N 33/02* (2006.01)

(52) U.S. Cl.
CPC .......... *G06T 7/0004* (2013.01); *A01G 18/00* (2018.02); *G01N 33/02* (2013.01); *G06T 7/97* (2017.01);
(Continued)

(58) Field of Classification Search
None
See application file for complete search history.

(56) References Cited

U.S. PATENT DOCUMENTS

| | | |
|---|---|---|
| 5,058,368 A | 10/1991 | Wheeler |
| 5,471,827 A | 12/1995 | Janssen et al. |

(Continued)

FOREIGN PATENT DOCUMENTS

| | | |
|---|---|---|
| CA | 2943302 A1 | 11/2015 |
| EP | 1220121 A1 | 7/2002 |
| NL | 8600887 A | 11/1987 |

OTHER PUBLICATIONS

Extended European Search Report dated Jul. 26, 2021 on European Application 18888666.7.

(Continued)

*Primary Examiner* — Delomia L Gilliard
(74) *Attorney, Agent, or Firm* — Brunet & Co., Ltd.; Hans Koenig; Robert Brunet (57) ABSTRACT A method of determining ripeness of a growing mushroom involves obtaining a sequence of images of a growing mushroom over a period of time and, from the sequence of images, measuring one or more features of the growing mushroom to obtain temporal measurements for the one or more features. The temporal measurements indicate rates at which the one or more features are changing. The temporal measurements are compared to pre-determined ripeness functions to determine the ripeness of the mushroom. The mushroom is picked if the comparison indicates that the mushroom is ready to be harvested.

22 Claims, 6 Drawing Sheets (52) U.S. Cl.
CPC ............... *G06T 2207/10016* (2013.01); *G06T 2207/10024* (2013.01); *G06T 2207/10048* (2013.01); *G06T 2207/30128* (2013.01)

(56) References Cited

U.S. PATENT DOCUMENTS

| | | | |
|---|---|---|---|
| 6,276,536 | B1 | 8/2001 | Terasaki et al. |
| 8,033,087 | B2 | 10/2011 | Rapila et al. |
| 2005/0196037 | A1* | 9/2005 | Muenzenmayer ..... G06V 10/25 382/164 |
| 2005/0268587 | A1 | 12/2005 | McKeown |
| 2007/0079644 | A1 | 4/2007 | Clark |
| 2012/0247007 | A1* | 10/2012 | Verdellen ............. B65D 85/345 47/1.1 |
| 2012/0286046 | A1* | 11/2012 | Ciurczak ............... G01J 3/2803 235/494 |
| 2014/0122044 | A1 | 5/2014 | Yasukawa |
| 2015/0044098 | A1* | 2/2015 | Smart .................. G01J 3/0267 422/82.05 |
| 2017/0032258 | A1* | 2/2017 | Miresmailli ........... G06N 20/00 |
| 2017/0042095 | A1* | 2/2017 | Van De Vegte ....... B25J 9/1697 |
| 2018/0081522 | A1* | 3/2018 | Greenberg ............ G06F 3/0484 |
| 2020/0107504 | A1* | 4/2020 | Bongartz ............... A01G 7/045 |
| 2020/0344965 | A1* | 11/2020 | Song ........................ A01G 7/00 |

OTHER PUBLICATIONS

Kim MS, et al. Sems. & Instrumen. Food Qual. (2011) 5:155-164.
International Search Report and Written Opinion dated Dec. 12, 2018 on PCT/CA2018/051580.
Fuzzy expert systems. Chapter 4, Edith Cowan University, Course Title U65, 2017. https://www.coursehero.com/file/25035305/Chapter4-L22pdf/.
A. Masoudian. Computer Vision Algorithms for an Automated Harvester. M.Sc. Thesis, 2013. Electrical and Computer Engineering, The University of Western Ontario.
MobiChamp. Mobile Harvesting Solutions. Internet extract http://www.mobichamp.nl (Nov. 1, 2017).
Mollazade K, et al. Computers and Electronics in Agriculture 98 (2013) 34-45.

* cited by examiner

METHODS AND SYSTEMS RELATED TO MUSHROOM RIPENESS DETERMINATION

CROSS-REFERENCE TO RELATED APPLICATIONS

This application is a national entry of PCT/CA2018/051580 filed Dec. 12, 2018 and claims the benefit of United States Provisional Patent Application U.S. Ser. No. 62/599,225 filed Dec. 15, 2017, the entire contents of both of which are herein incorporated by reference.

FIELD

This application relates to cultivation and harvesting of mushrooms, in particular to methods and systems of determining ripeness of a growing mushroom for determining when the growing mushroom is ready to harvest.

BACKGROUND

Mushrooms (*Agaricus bisporus*) are a very fast growing year-round crop. The harvesting cycle of mushrooms is three to five days with four to six harvesting rounds daily. Harvesting of mushrooms for the fresh market is generally done by hand, where harvesters are trained to select and pick mushrooms that are ready for harvesting at each harvesting round. The selection process is significantly more complex than just picking large-sized mushrooms. In addition to geometrical and clustering based considerations, high quality mushrooms for the fresh market must be harvested at the right maturity/ripeness level. Two mushrooms with the same size could have different maturity levels, where one of them should be harvested to avoid quality deterioration, while the other should be left to grow into a bigger size, to maximize yield. Accordingly, accurate and consistent assessment of mushroom ripeness is important for effective harvesting of mushrooms.

In determining mushroom ripeness, the harvesters typically look at features such as color brightness, firmness (which is typically visually assessed), shape, size and stem length (if the stem is visible). Assessing ripeness is a challenging task, especially because mushrooms are a delicate produce, which is not supposed to be contacted/touched for assessing firmness (one of the important ripeness indicators). Accordingly, the challenging nature of ripeness assessment, and the diversity in expertise (training and experience) among the harvesters lead to one or more of the following problems:

1. Wasted time and cost for training. Much training and practice are required for human harvesters to be able to assess mushrooms ripeness. A new harvester requires at least three months to be considered fully trained.
2. Wasted time in ripeness assessment. Properly assessing ripeness requires a considerable amount of time for decision making and harvesting of mushrooms.
3. Compromised quality due to contact-based ripeness assessment. Frequently, harvesters touch and feel mushrooms in order to assess ripeness (based on firmness). Frequent touching of mushrooms during growth increases the chance of disease, and also causes bruises/discoloration, which reduces mushroom quality.
4. Compromised yield and quality due to lack of experience/skills. Quality of harvested mushrooms is compromised due to inaccurate assessment of ripeness. Many unripe mushrooms are mistakenly harvested before they ripe (compromised yield) and others are not harvested on time and left to overripe (compromised quality).
5. Compromised harvesting yield and quality due to inconsistency of decisions even by well-trained harvesters. Inconsistency in ripeness assessment by well-trained harvesters occurs for many reasons, including difficulty of contactless assessment, labor fatigue, limitations on time allocated for assessment/harvesting and limitation on field of view (eye sight), especially at the middle of shelves.
6. Impeding the development of an automated harvesting solution. One of the reasons an automated mushroom harvesting solution has not been widely implemented is the lack of an objective and contactless mushroom ripeness assessment method.

There are various methods in the art, which use cameras for locating and measuring cap diameters of mushrooms among other current mushroom features in a mushroom bed before harvesting the mushrooms with a mechanical picker. However, such methods do not provide for automatically selecting and picking mushrooms based on ripeness considerations. There remains a need for an automated consistent and contactless mushroom ripeness assessment system that can make or support optimized harvesting decisions.

SUMMARY

A method of determining ripeness of a growing mushroom involves obtaining a sequence of images of a growing mushroom over a period of time and, from the sequence of images, measuring one or more features of the growing mushroom to obtain temporal measurements for the one or more features. The temporal measurements indicate rates at which the one or more features are changing. The temporal measurements are compared to pre-determined ripeness functions to determine the ripeness of the mushroom. The mushroom is picked if the comparison indicates that the mushroom is ready to be harvested.

Thus, in one aspect, there is provided a method of determining ripeness of a growing mushroom, the method comprising: obtaining a sequence of images of a growing mushroom over a period of time; from the sequence of images, measuring one or more features of the growing mushroom to obtain temporal measurements for the one or more features of the growing mushroom, the temporal measurements indicating rates at which the one or more features are changing; and, comparing the temporal measurements for the one or more features to pre-determined ripeness functions for each of the temporal measurements to determine the ripeness of the mushroom.

In another aspect, there is provided a method of harvesting a growing mushroom, the method comprising: determining ripeness of the growing mushroom by a method as defined above; and, picking the growing mushroom if the comparing of the temporal measurements for the one or more features to the pre-determined ripeness functions for each of the temporal measurements indicates that the growing mushroom is ready to be harvested.

In another aspect, there is provided a system for determining ripeness of a growing mushroom, the system comprising: one or more imaging devices for obtaining a sequence of images of a growing mushroom over a period of time; and, a computer operatively connected to the one or more imaging devices, the computer configured to receive image data from the one or more imaging devices, the computer programmed to measure from the image data one or more features of the growing mushroom to obtain temporal measurements for the one or more features, the temporal measurements indicating rates at which the one or more features are changing, and compare the temporal measurements for the one or more features to pre-determined ripeness functions for each of the temporal measurements to determine the ripeness of the mushroom.

The present methods and systems provide for an automated consistent and contactless mushroom ripeness assessment, which can make or support optimized harvesting decisions, particularly for making or supporting harvesting decisions on live, still growing mushrooms. The methods and systems involve ripeness assessment by analyzing computer vision data. Visioning systems of the prior art have used point-in-time data (i.e. current or immediate measurements) to make harvesting decisions. In the present methods and systems, determination of the ripeness is based on temporal data acquired through the computer vision. The temporal data provides information on how fast a feature of the growing mushroom is changing, not just an immediate absolute measurement of a feature. How fast a feature of the growing mushroom changes provides a rate of change of the mushroom feature, which may be compared to a pre-determined rate of change function for that mushroom feature, the pre-determined rate of change function correlating to a ripeness level of the growing mushroom. For greater accuracy and certainty, temporal data for more than one mushroom feature may be collected, analyzed and compared to pre-determined ripeness functions for each mushroom feature. The growing mushroom may be picked if the comparing of the temporal measurements for the one or more features to the pre-determined ripeness functions for each of the temporal measurements indicates that the growing mushroom is ready to be harvested. Information about the absolute value at a given time (i.e. current or immediate measurements) of a mushroom feature may be incorporated into the analysis to assist with harvesting decisions, but it is the ripeness assessment based on temporal measurements that greatly enhances accuracy of the harvesting decisions.

The methods and systems may be implemented through a semi-automated harvesting system, a fully automated harvesting system or a hybrid of both systems. The methods and systems may be incorporated as a supplementary module within an existing mushroom harvesting decision support system.

The present methods and systems offer one or more advantages. Automated ripeness assessment reduces the need for harvesters to make decisions on harvesting; therefore, no training for ripeness assessment is required. Automated decision support may make ripeness decisions much faster than humans. Data capture through computer vision is contactless; therefore, no contact-based assessments occur, reducing loss of quality due to human contact with the mushrooms. If trained properly, decisions on ripeness made by the automated system are at least as good as a human expert, eliminating differences in the level of skill among human decision makers. Decisions made by automated ripeness assessment are consistent, and are not influenced by the state of a human mind, thereby leading to consistent mushroom quality. Vision-based data collection and automated decision making facilitates guided harvesting and robotic harvesting.

Further features will be described or will become apparent in the course of the following detailed description. It should be understood that each feature described herein may be utilized in any combination with any one or more of the other described features, and that each feature does not necessarily rely on the presence of another feature except where evident to one of skill in the art.

BRIEF DESCRIPTION OF THE DRAWINGS

For clearer understanding, preferred embodiments will now be described in detail by way of example, with reference to the accompanying drawings, in which.

DETAILED DESCRIPTION

The methods and systems described herein involve ripeness-based harvesting of mushrooms (*Agaricus bisporus*) using computer-assisted vision-based data acquisition and processing. Ripeness of the mushrooms is assessed using temporal measurements of one or more features of a growing mushroom.

A temporal measurement is a measurement of how fast a feature of the growing mushroom is changing, i.e. the rate of change of the feature. At any given point in time, the rate of change of a feature may be determined by the slope of a tangent to a curve plotting time vs. the absolute value of the feature. The term "temporal feature" may be used to indicate a rate of change of a mushroom feature. In contrast, a current or immediate measurement is a measurement of the absolute value of a feature at a single point in time. The term "current feature" may be used to indicate the absolute value of a feature at a single point in time.

There is no universally agreed upon objective measure for ripeness of a mushroom. Standards may be different from growing operation to growing operation. However, in any given instance, a pre-determined ripeness function may be established for each of one or more features of the mushroom (for temporal features or for both temporal and current features), the pre-determined ripeness functions for each of the one or more mushroom features acting as indicators of when the mushroom is ready to be harvested. For temporal measurements, the pre-determined ripeness function is a pre-determined rate of change function, while for current measurements, the pre-determined ripeness threshold is a pre-determined absolute value function. While the pre-determined ripeness functions may be arbitrary in the sense of not being universally accepted, the pre-determined ripeness functions may be established for a given mushroom growing operation based on customer acceptance or other criteria.

The one or more mushroom features may include, for example, one or more of mushroom height, cap diameter, cap curvature, cap misshapenness, color brightness, temperature and hyperspectral reflectance response. Other mushroom features may be measured.

Temporal measurements may include, for example, one or more of growth rate, color brightness change, temperature change, change in hyperspectral reflectance response or ratios thereof. Growth rate, temperature change and change in hyperspectral reflectance response are particularly useful temporal measurements leading to greater accuracy and consistency in ripeness determination. Growth rate may comprise rate of change of mushroom height, rate of change of cap diameter, rate of change of cap curvature, rate of change of cap misshapenness or ratios thereof. In one embodiment, temporal measurement of the growth rate comprises measurement of the rate of change of cap diameter, the rate of change of mushroom height or both. Change in hyperspectral reflectance response may comprise a change in intensity at a short-wave infrared (SWIR) wavelength (i.e. a hyperspectral wavelength). In one embodiment, the SWIR wavelength may have a value in a range of 1325-1500 nm, preferably 1375-1475 nm. More preferably, the SWIR wavelength is about 1450 nm. In another embodiment, the SWIR wavelength may have a value in a range of 1875-2000 nm, preferably 1900-1975 nm. More preferably, the SWIR wavelength is about 1950 nm. Reflectance at one or more SWIR wavelengths may be useful for obtaining a temporal measurement.

Ripeness of a mushroom is determined by comparing the temporal measurements to pre-determined ripeness functions. Comparisons may be made individually for each temporal measurement against an individual pre-determined ripeness function for that temporal measurement. A harvesting decision may then be made based on one or more of the comparisons. Where there is disagreement between the temporal measurements as to whether the mushroom is ripe enough to harvest, the harvesting decision may rely on a favored temporal measurement (e.g. rate of growth of cap diameter and/or height, or change in hyperspectral reflectance response), or a consensus approach may be used to resolve the disagreement. In a consensus approach, the decision selected would have the greatest consensus among the considered temporal measurements.

The pre-determined ripeness functions for each of the temporal measurements may be embodied in a single pre-determined ripeness threshold for all of the temporal measurements. The single pre-determined ripeness threshold may be defined in a common ripeness scale for any combination of temporal measurements. The range of values obtainable from each temporal measurement may be assigned ripeness values on a common scale that correspond to levels of ripeness of the mushroom, and the single pre-determined ripeness threshold may be defined based on the common scale.

The system may comprise both hardware and software components. Hardware components comprise one or more imaging devices, for example cameras, spectrometers or the like. The cameras may be visual light cameras (2-D and/or 3-D), thermal cameras (i.e. long-wave infrared (LWIR) cameras) and/or multi-spectral cameras (i.e. hyperspectral or short-wave infrared (SWIR) cameras). Preferably, the imaging devices comprise at least a 2-D visual light camera. The one or more imaging devices may be mounted in a mushroom growing facility to provide a good view of the mushroom growing on mushroom compost. The one or more imaging devices may be mounted on one or more mobile units, for example battery-powered carts, that travel between shelves on which the growing mushrooms are supported. In a typical mushroom growing facility, the mushroom growing compost is supported on metal shelves. The shelves may be equipped with guide rails between the shelves on which the mobile units may travel along a shelf. The one or more imaging devices extract data on mushroom features over time.

Control software for performing the methods may be embodied in a control apparatus operatively linked to, for example in electronic communication with, the one or more imaging devices. The control apparatus may also be operatively linked to other hardware components of an overall harvesting operation, for example robotic pickers, climate control devices (e.g. ventilation systems including one or more of humidifiers, heaters, fans, etc.), various sensors and the like. Electronic communication may be provided through wires or wirelessly. The control apparatus may comprise, for example, a computer, an output device and an input device, the computer comprising a microprocessor for controlling operations and a non-transient electronic storage medium for storing information about the mushrooms and bed and/or for storing computer executable code for carrying out instructions for implementing the method. The computer may further comprise a transient memory (e.g. random access memory (RAM)) accessible to the microprocessor while executing the code. A plurality of computer-based apparatuses may be connected to one another over a computer network system and geographically distributed. One or more of the computer-based apparatuses in the computer network system may comprise a microprocessor for controlling operations and a non-transient electronic storage medium for storing information about the mushrooms and/or for storing computer executable code for carrying out instructions for implementing the method, and the computer-based apparatuses in the network may interact so that the method may be carried out automatically from remote locations. The output device may be a monitor, a printer, a device that interfaces with a remote output device or the like. The input device may be a keyboard, a mouse, a microphone, a device that interfaces with a remote input device or the like. With a computer, data (e.g. images from imaging devices) may be a graphically displayed in the output device. There is also provided a computer readable non-transient storage medium having computer readable code stored thereon for executing computer executable instructions for carrying out the method.

The system may be integrated with current mushroom production practices and infrastructure (e.g. metal Dutch shelving). The system may also be integrated into an existing harvesting decision support system that is currently based only on geometry and clustering considerations. Accordingly, the system could be utilized in semi-automated harvesting solutions, fully automated harvesting solutions or hybrid (collaborative) harvesting solutions. In a semi-automated solution, light may be used to highlight to human harvesters the mushrooms to be picked, a light projector (e.g. a light emitting diode or laser light projector) mounted to the same structure (e.g. a cart) used to carry the imaging devices for data acquisition. In a fully automated solution, a robotic harvester equipped with one or more suction cups could execute the harvesting decisions made by the ripeness assessment system. In a hybrid solution, humans and collaborative robots may work together to execute the harvesting decisions, humans picking the small mushrooms that may be harder to pick with suction cups in thinning (separation) harvesting, and robots doing the harvesting during graze picking, which is a mechanically less challenging harvesting task.

EXAMPLES

Experimental Results:

Experiments were performed revealing that temporal measurements of mushroom features are better correlated to ripeness than current measurements (i.e. absolute values) of the features at any given time.

Ripeness Scale

In the experiments, correlation of mushroom temporal measurements to mushroom ripeness was done in view of a ripeness scale used by mushroom harvesting experts who harvest mushrooms manually. Manual mushroom harvesters assess mushroom ripeness on a scale from 1 to 5. A very firm and immature mushroom would have a ripeness value of 1, while a very soft and completely open mushroom would have a ripeness value of 5. According to the ripeness scale, mushrooms start to over-ripen at a ripeness value of 3.5. Table 1 lists characterizing attributes for each ripeness value.

TABLE 1

| Ripeness Value | Characterizing Attributes | Ripeness Level |
|---|---|---|
| 1 | Very stiff/firm mushroom cap, very bright (white). These are usually small buttons in the very early stages of growth. | Under-ripe |
| 1.5 | Similar to the previous category. May just demonstrate slightly less stiffness/firmness. | Under-ripe |
| 2 | Demonstrates very early signs of springiness in the cap. Slightly reduced brightness (whiteness). | Under-ripe |
| 2.5 | Similar to the previous category. With slightly more springiness in the cap | Under-ripe |
| 3 | Demonstrates some elasticity/springiness, but not soft, and is still fairly white. | Just Ripe |
| 3.5 | Shows early signs of softness and discoloration. Could also show early signs of a stretched veil. | Marginally Ripe |
| 4 | Stretched and about to open veil. Soft cap with noticeable discoloration. | Over-ripe |
| 4.5 | Very stretched veil or partially open soft cap. It also shows major discoloration and color inconsistency. | Over-ripe |
| 5 | Completely open veil and very soft and dry cap. Far from being bright or white. | Over-ripe |

For a more quantitative characterization of each ripeness value, radial mushroom firmness values were also measured and a typical range was assigned to each ripeness value. The firmness values were experimentally obtained using a texture analyzer that records the force at various displacements of a flat steel disc that is applied towards the radial direction of the mushrooms cap. The maximum displacement of the disc was set to 3 mm. The firmness is given by the slope of the linear part of the resulting force-displacement curve. The firmness value for each mushroom is the average of the firmness values recorded at three equally spaced points. Table 2 shows typical approximate firmness ranges, experimentally found, for each ripeness value.

TABLE 2

| Ripeness | Firmness range (Force/Displacement (N/mm)) | |
|---|---|---|
| Value | From | To |
| 1 | Greater than or equal 5 | — |
| 1.5 | Greater than or equal 4.5 | Less than 5 |
| 2 | Greater than or equal 4 | Less than 4.5 |
| 2.5 | Greater than or equal 3.5 | Less than 4 |
| 3 | Greater than or equal 3 | Less than 3.5 |
| 3.5 | Greater than or equal 2.5 | Less than 3 |
| 4 | Greater than or equal 2 | Less than 2.5 |
| 4.5 | Greater than or equal 1.5 | Less than 2 |
| 5 | — | Less than 1.5 |

Correlation of Size and Height Change to Ripeness

Figure 1A:
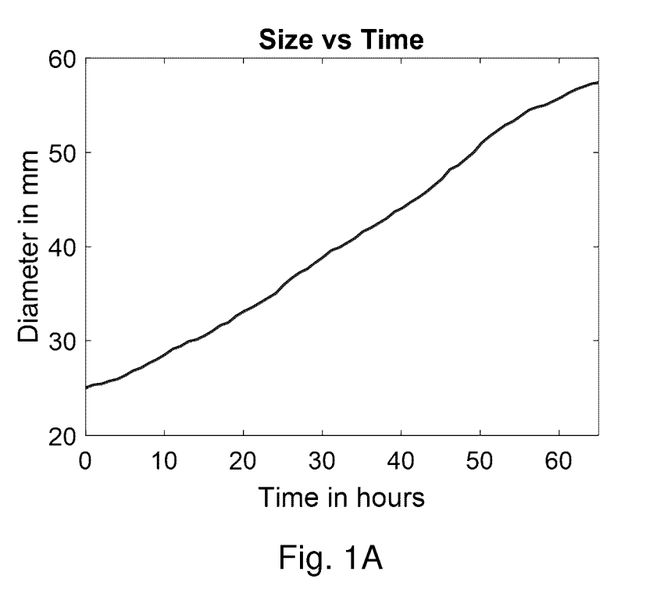
FIG. 1A is a graph showing change in mushroom cap diameter (mm) as a function of growing time (hr).
Figure 1B:
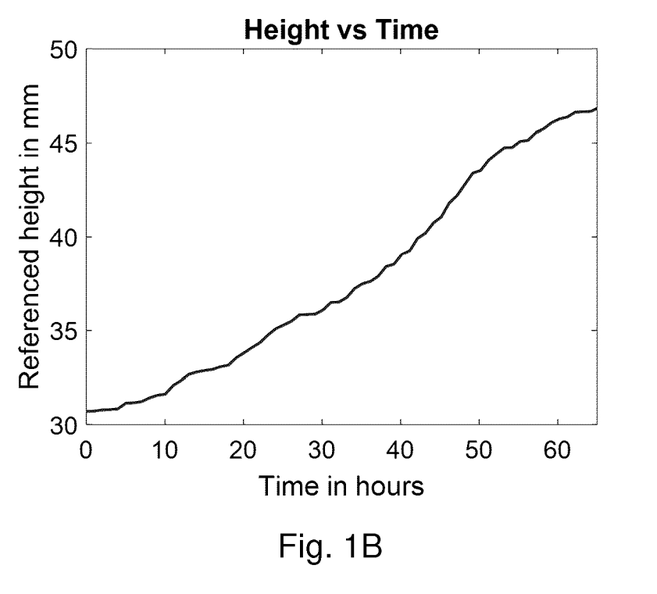
FIG. 1B is a graph showing change in mushroom height (mm) as a function of growing time (hr).

The rate of change of mushroom cap diameter (size) and mushroom height (height) over time during mushroom growth correlates with mushroom ripeness. Mushrooms start growing in cap diameter and height at a slow rate and as time progresses, the growth rate for cap diameter and height starts to increase. As mushrooms approach the end of the growth cycle, the rate of increase of the cap diameter and height begins to slow again. Plotting the cap diameter or height vs. growing time produces a sigmoidal curve having an inflection point. Ripeness was found to be correlated with early signs of decline in the rate of growth. FIG. 1A and FIG. 1B show examples of graphs using real data (65 points of data). FIG. 1A shows change in mushroom cap diameter (mm) as a function of growing time (hr), while FIG. 1B shows change in mushroom height (mm) as a function of growing time (hr). In both cases, after about 50 hours of growth, the rates of increase in cap diameter and height of the mushroom were starting to slow, and the mushroom was just ripe as determined by firmness measurement against the ripeness scale described above.

While the data is shown graphically, the data may be numerically analyzed by calculating the instantaneous slopes for time points on the curves. Thus, temporal measurement of cap diameter is given by the slope of the diameter change for the last eight data acquisitions. A normalized value is obtained by multiplying by 50 (an assumed nominal value for the diameter) and dividing by the current diameter value. Likewise, the temporal measurement of height is given by the slope of the height change for the last eight data acquisitions. All the height values are measured relative to an imaginary plane in order to eliminate the effect of compost surface unevenness. The normalized value is obtained by multiplying by 50 (an assumed nominal value for the diameter) and dividing by the current diameter value.

Correlation of Temperature Change to Ripeness

Figure 2:
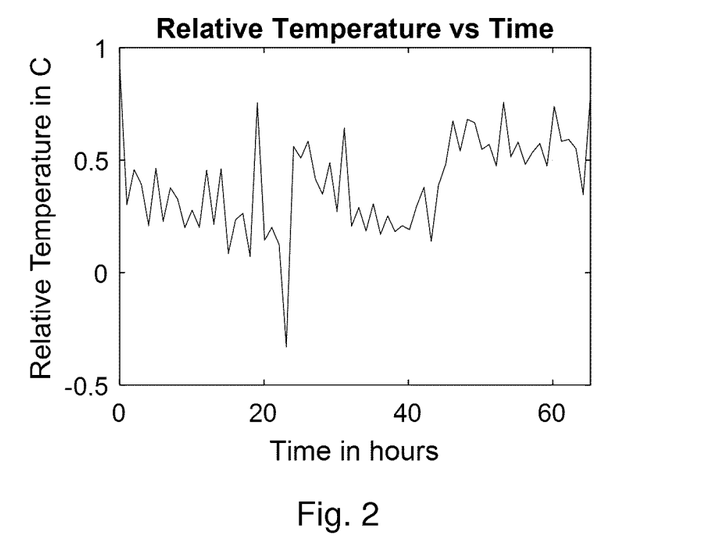
FIG. 2 is a graph showing change in mushroom temperature (° C.) as a function of growing time (hr).

The rate of change of mushroom temperature has a similar behavior to height and size. Mushrooms start the growing cycle having a low temperature change rate and as time progresses, the mushrooms start to become more metabolically active and their temperature rapidly increases until reaching a peak. As the mushrooms approach the end of the growing cycle, the rate of temperature increase drops again, signifying that the mushroom has ripened. Ripeness was also found to be correlated with signs of decline in the rate of temperature increase. FIG. 2 shows an example of a graph using real data. FIG. 2 shows change in temperature (° C.) as a function of growing time (hr). After about 50 hours of growth, the rate of temperature increase of the mushroom started to slow, and the mushroom was just ripe as determined by firmness measurement against the ripeness scale described above.

Temporal measurement of temperature is given by the ratio between the $10^{th}$ percentile of the temperatures a mushroom has reached so far (representing maximum relative temperature) to the average temperature of the last eight acquisitions. Each temperature value for each mushroom is measured relative to an external reference object.

Correlation of Color Brightness Change to Ripeness

Figure 3:
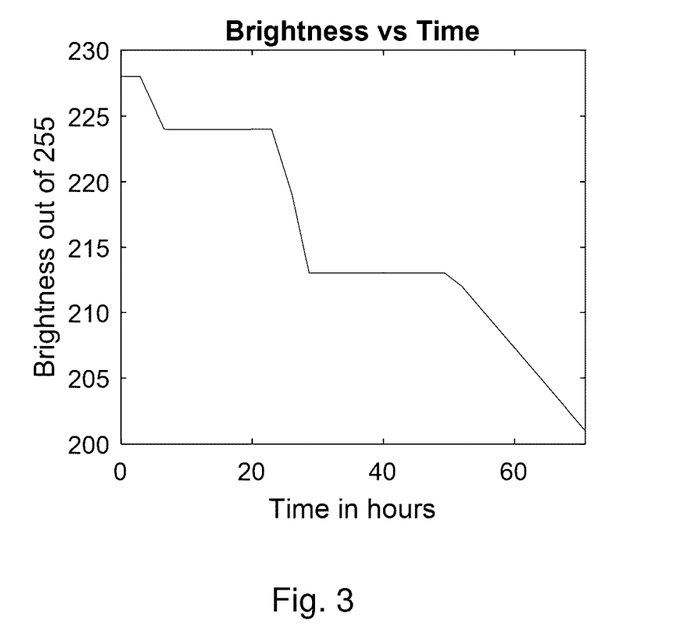
FIG. 3 is a graph showing change in mushroom brightness as a function of growing time (hr).

When mushrooms start the growing cycle, they have a very bright color. Brightness level goes down as mushrooms grow. The rate by which the brightness level decreases is slow at the beginning of the growing cycle, but the rate of change of brightness level accelerates as the mushroom matures. Ripeness was also found to be correlated with signs of rapid decline in the rate of brightness decrease. FIG. 3 shows an example of a graph using real data. FIG. 3 shows change in brightness as a function of growing time (hr). After about 50 hours of growth, the rate of decrease in brightness of the mushroom started to accelerate, and the mushroom was just ripe as determined by firmness measurement against the ripeness scale described above.

Temporal measurement of color brightness is given by the ratio between the average of the last eight acquisitions and the $90^{th}$ percentile (the $90^{th}$ percentile represents the maximum brightness). The measured brightness values are normalized with respect to an external white reference object (in the field of view of the imaging device) in order to provide more consistent brightness measurements in variable lighting conditions. In processing the collected data, it was assumed that brightness can only decrease and cannot increase; therefore, the curve in FIG. 3 is rectified.

Correlation of Hyperspectral Bands to Ripeness

Mushroom ripeness also correlates to non-visual light bands (hyperspectral bands). A band is a tight range of wavelengths. Multiple rounds of experiments and analyses have confirmed that mushroom ripeness is strongly correlated to two specific non-visual light bands, one band is around 1450 nm and another band is around 1950 nm. The two bands are in the short-wave infrared (SWIR) region of the electromagnetic spectrum. The two bands are known in the scientific literature for their correlation to water absorption.

Figure 4A:
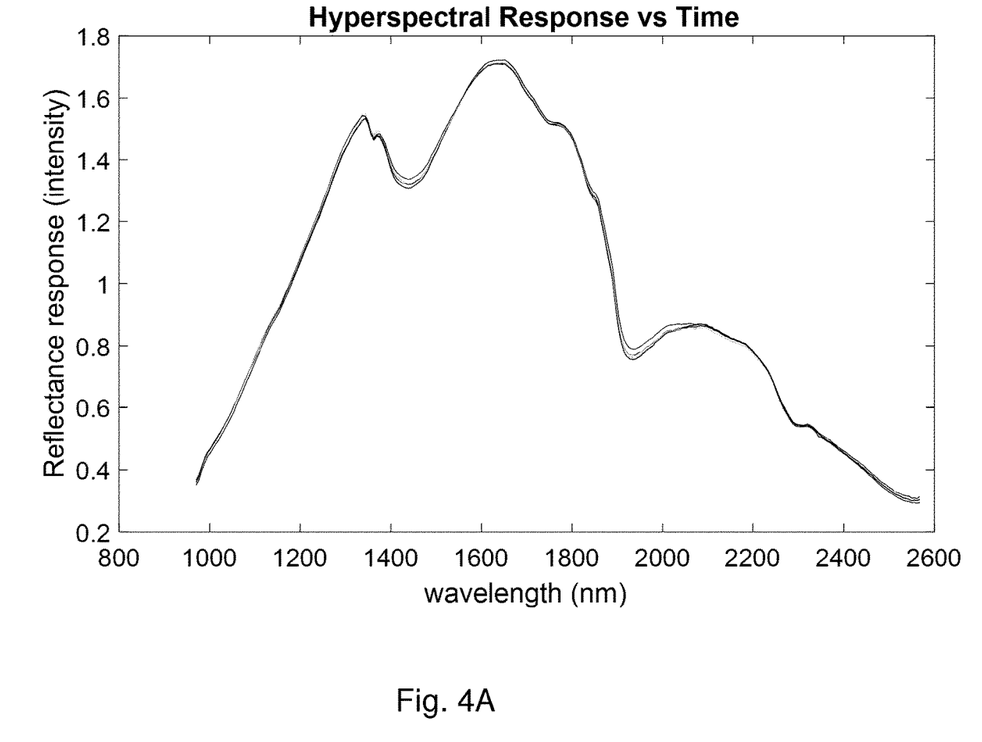
FIG. 4A is a graph of hyperspectral reflectance response (Intensity) as a function of wavelength (nm) for a mushroom. The graph has five curves thereon representing hyperspectral measurements taken for the mushroom at five different stages of growth to illustrate changes over time.
Figure 4B:
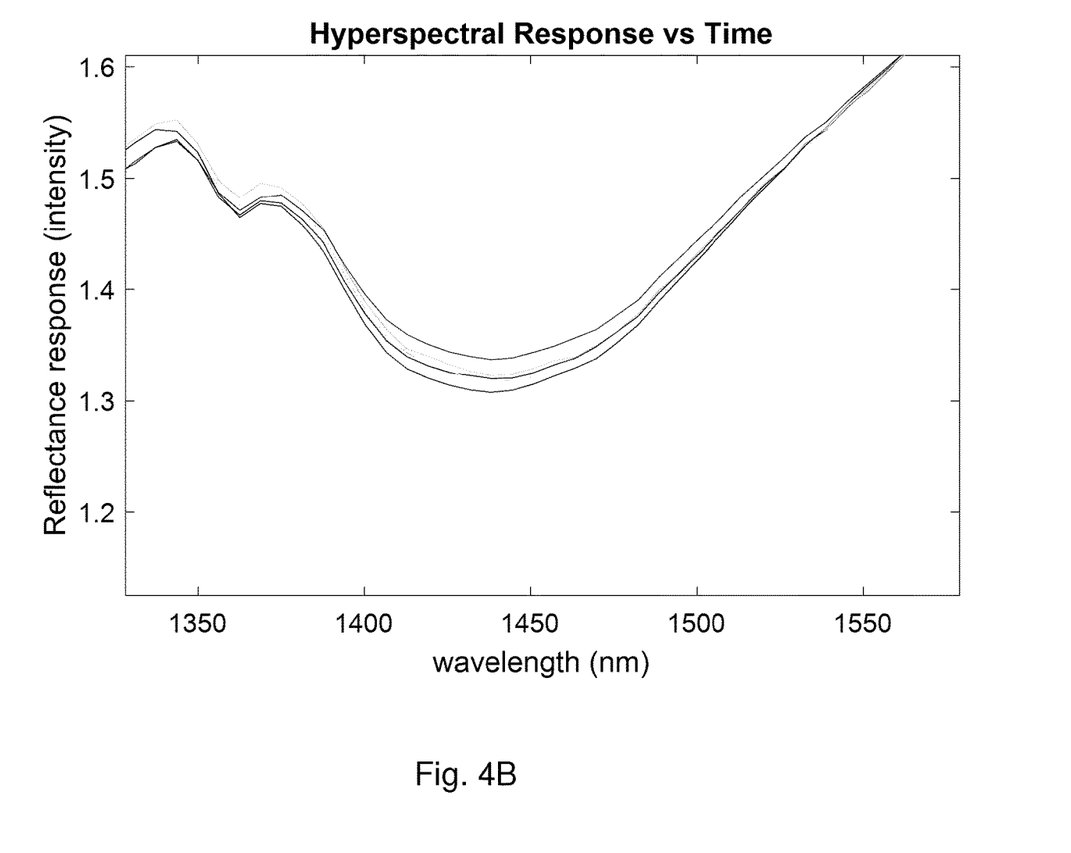
FIG. 4B is a magnified view of FIG. 4A between 1325 nm and 1575 nm.

FIG. 4A and FIG. 4B show hyperspectral data analysis for the same mushroom at different stages of growth. The x-axis represents light wavelength (nm) and the y-axis represents light intensity. A significant difference in light intensity between the curves at specific wavelengths may imply a correlation between mushroom ripeness and the intensity of light at those wavelengths. FIG. 4A shows two bands (around 1450 nm and around 1950 nm), which have been found to correlate with mushroom ripeness. FIG. 4B is a magnified view of the band around 1450 nm. Each of the five individual curves in FIG. 4A and FIG. 4B represents a different hyperspectral data acquisition in time. Data acquisition was performed over the following time course: Day 1 at 4:00 pm; Day 2 at 3:00 pm; Day 3 at 11:00 am; Day 3 at 3:00 pm; and, Day 4 at 11:00 am. In FIG. 4A and FIG. 4B, the higher the curve at the wavelength (1450 nm or 1950 nm), the later the acquisition was made. Thus, the five curves ordered from lowest to highest in FIG. 4A and FIG. 4B reflect the sequence of the time course from Day 1 to Day 4 provided above.

Temporal reflectance response measurement is given by the slope of the Reflectance Ratio for the given wavelength for the last eight data acquisitions. The Reflectance Ratio for a given wavelength is the reflectance at the wavelength of interest divided by the reflectance at another distinctive wavelength (peak or a valley). For example, the Reflectance Ratio used for the 1450 nm wavelength is given by R(1459)/R(1653), where R(1459) is the reflectance at 1459 nm (about 1450 nm) and R(1653) is the reflectance at 1653 nm (the peak to the right in FIG. 4A).

Figure 4C:
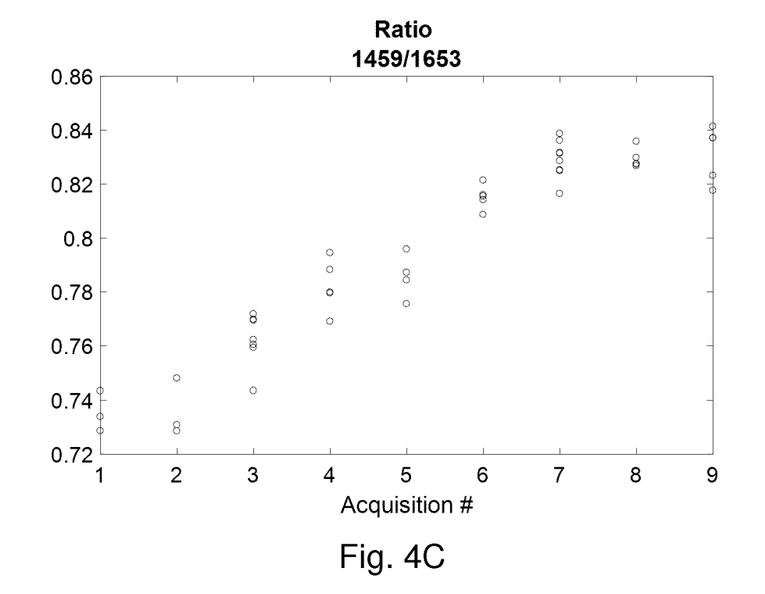
FIG. 4C is a graph of Hyperspectral Reflectance Ratio (R(1459)/R(1653)) as a function of data acquisition number (time) for a hyperspectral wavelength around 1450 nm for a mushroom.
Figure 4D:
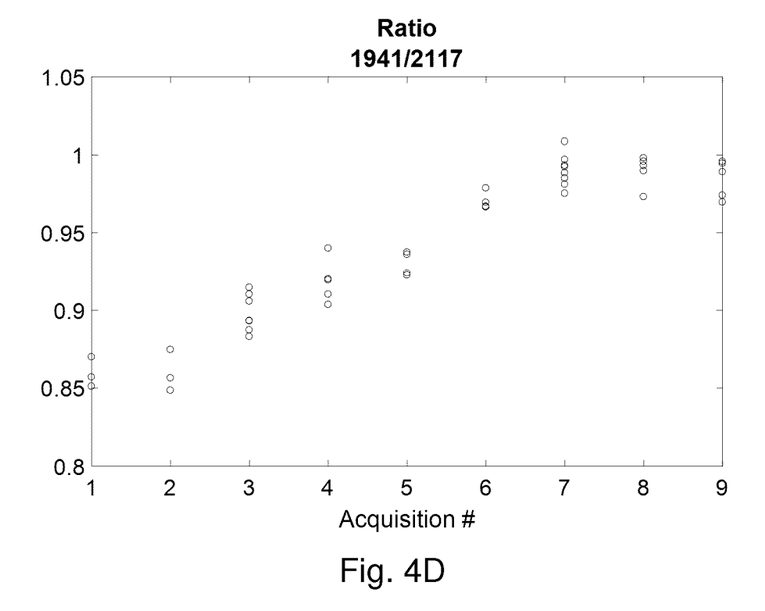
FIG. 4D is a graph of Hyperspectral Reflectance Ratio (R(1941)/R(2117)) as a function of data acquisition number (time) for a hyperspectral wavelength around 1950 nm for a mushroom.

FIG. 4C and FIG. 4D graphically represent the temporal reflectance response of the growing mushroom around the 1450 nm and 1950 nm hyperspectral bands, respectively. FIG. 4C depicts Hyperspectral Reflectance Ratio vs. data acquisition number (time) for the 1450 nm hyperspectral band, while FIG. 4D depicts Hyperspectral Reflectance Ratio vs. data acquisition number (time) for the 1950 nm hyperspectral band.

Operating the System and Method:

Based on the experimental results, a ripeness assessment system and method were developed. The system and method involve acquiring mushroom images in predetermined time intervals using one or more imaging devices, for example a 2-D camera, a 3-D camera (3-D vision and/or with time-of-flight sensor technology), a 3-D laser scanner, a Long Wave Infra Red (LWIR) camera (also known as thermal camera) and/or a Short Wave Infra Red (SWIR) camera, (also known as a hyperspectral or multi-spectral camera). The system and method can operate with just one camera, for example a 2-D camera; however, further accuracy and reliability are realized by the addition of other cameras. Highest accuracy and reliability are achieved when the data from many different cameras are utilized. The cameras are mounted on a battery powered mobile cart that moves on guided rails mounted between the metal shelves, where mushrooms grow.

At each round of image acquisition, the images are processed and the system extracts mushroom features and tracks changes in the features over time. The features include: mushroom cap diameter, height, color brightness, temperature, and reflectance response (intensity) at a specific SWIR wavelength. The temporal behaviour for each feature is defined above.

Several rounds of experiments (data collection and data analysis) were carried out to characterize the relationship between mushroom ripeness and mushroom features in terms of ripeness functions. Using the collected data, ripeness values were classified into two levels: low (between 1 and 3) and high (between 3.5 and 5), in accordance with the ripeness levels defined in Table 1. For each ripeness level and each feature, the mean and the standard deviation values for that feature was calculated.

Ripeness status of mushrooms is identified from the temporal behaviour of the mushroom features using a Consensus Fuzzy Logic model. The Fuzzy Logic model was developed in order to find the corresponding ripeness value (a continuous value between 1 and 5) for any given combination of feature measurements. The Fuzzy Logic model relies on ripeness functions, specifically ripeness membership functions, which are mathematical functions that express the relationship between the value of a give feature measurement and the ripeness level. In the model, these membership functions are expressed through the mean and the standard deviation values mentioned above (Gaussian functions). For instance, it was found, from the collected data that the mean and standard deviation values for the temporal temperature values corresponding to the high ripeness category are 0.91 and 0.023. Therefore, for any given mushroom, the closer the temporal temperature value is to 0.91, the closer that mushroom is to the mean value of the high ripeness class. The 0.91 is a relatively low value compared to the mean temporal temperature value for the low ripeness class which is 0.94. This shows an inverse relationship between the temporal temperature and the ripeness.

The Fuzzy Logic model handles the direction of relationships between inputs and outputs through Fuzzy Logic rules. Fuzzy Logic rules are extracted and embedded in the Fuzzy Logic model based on the behavior observed in the collected data. The model is a consensus Fuzzy Logic model. When multiple input features are being considered, it is probable there is not full agreement between all the features on the ripeness level. When not all of the features lead to the same ripeness decision, the decision is selected which has the greatest consensus among the considered features. For example, if there are three input features being considered by the model: Temporal Size, Temporal Height and Temporal Temperature, then the Fuzzy Logic Rules, following the above-mentioned consensus approach, would be as follow:

If Temporal Size is low & Temporal Height is low, then Ripeness Level is high

If Temporal Size is low & Temporal Temperature is low, then Ripeness Level is high If Temporal Height is low & Temporal Temperature is low, then Ripeness Level is high If Temporal Size is low, Temporal Height is low, & Temporal Temperature is low, then Ripeness Level is high If Temporal Size is high & Temporal Height is high, then Ripeness Level is low If Temporal Size is high & Temporal Temperature is high, then Ripeness Level is low If Temporal Height is high & Temporal Temperature is high, then Ripeness Level is low If Temporal Size is high, Temporal Height is high, & Temporal Temperature is high, then Ripeness Level is low Table 3 provides the parameters of the membership functions for the ripeness and some of the features. The values in Table 3 were calculated after excluding outliers for each feature. The Gaussian function (normal distribution) was used to characterize all membership functions.

TABLE 3

| Feature | Level | Direction of Relationship | Min Value | Max Value | Mean | Stand. Deviation |
|---|---|---|---|---|---|---|
| Ripeness | Low | — | 1 | 5 | 2 | 0.65 |
| | High | | | | 3.8 | 0.46 |
| Size | Low | Direct | 15 | 70 | 48.7 | 7 |
| | High | | | | 54.2 | 6.2 |
| Temporal Color | Low | Inverse | 0 | 1 | 0.949 | 0.022 |
| | High | | | | 0.985 | 0.008 |
| Temporal Size | Low | Inverse | 0 | 1 | 0.36 | 0.1 |
| | High | | | | 0.6 | 0.18 |
| Temporal Height | Low | Inverse | 0 | 1 | 0.18 | 0.1 |
| | High | | | | 0.32 | 0.17 |
| Temporal Temperature | Low | Inverse | 0 | 1 | 0.91 | 0.023 |
| | High | | | | 0.94 | 0.034 |

When fed with the value for each feature value, the Consensus Fuzzy Logic model produces a single value for ripeness between 1 and 5, based on the predefined membership functions and Fuzzy Logic rules. To make a decision on any given mushroom, whether it is ripe or not, the calculated ripeness value is compared with a predefined ripeness threshold (typically between 3 and 3.5). If the calculated ripeness value is greater than the predefined ripeness threshold, then that mushroom is considered to be a ripe mushroom.

A change in environmental conditions, mainly temperature and relative humidity, will impact the rate of mushroom growth. To accommodate environmental conditions, three membership functions (mean and standard deviation) are identified for each feature: low, medium and high. Which membership functions to be considered for making the ripeness decision will depend on the general growth rate. The general growth rate is given by the overall average slope of the cap diameters of all the mushrooms. If the growth rate is low, then the low membership functions are considered, if the growth rate is medium, then the medium membership functions are considered and if the growth rate is high, then the high membership functions are considered.

Figure 5:
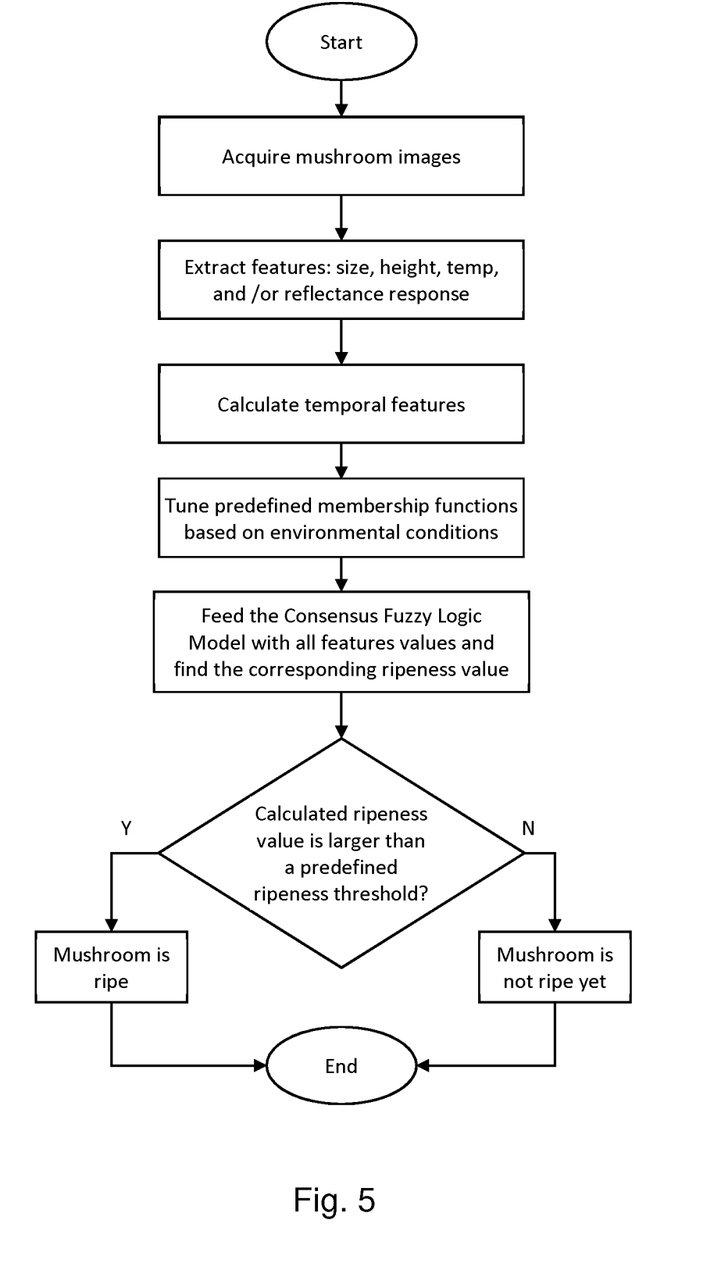
FIG. 5 is a flowchart summarizing a method of determining ripeness of a growing mushroom.

FIG. 5 depicts a flow chart that summarizes the main steps taken by the system and method in order to make ripeness decisions. Mushroom images are acquired over time while the mushrooms grow, and features are extracted from the images, for example mushroom size (cap diameter), height temperature and/or reflectance response. From the extracted features, temporal measurements for each mushroom feature are calculated using data from the sequence of images over time. As described above, pre-defined membership functions are tuned based on environmental conditions. Then, the Fuzzy Logic model is fed with all of the temporal feature measurements to obtain corresponding ripeness values. If the calculated ripeness of a mushroom is larger than a pre-defined ripeness threshold, then the mushroom is ripe and ready to be harvested. If the calculated ripeness of a mushroom is not larger than a pre-defined ripeness threshold, then the mushroom is not ripe and is permitted to grow further.

The novel features will become apparent to those of skill in the art upon examination of the description. It should be understood, however, that the scope of the claims should not be limited by the embodiments, but should be given the broadest interpretation consistent with the wording of the claims and the specification as a whole.

The invention claimed is:

1. A method of determining ripeness of a growing mushroom, the method comprising:
    obtaining a sequence of images of a growing mushroom over a period of time;
    from the sequence of images, measuring one or more features of the growing mushroom to obtain temporal measurements for the one or more features of the growing mushroom, the temporal measurements indicating rates at which the one or more features are changing; and,
    comparing the temporal measurements for the one or more features to pre-determined ripeness functions for each of the temporal measurements to determine the ripeness of the mushroom.

2. The method of claim 1, wherein the one or more temporal measurements comprises one or more of growth rate, color brightness change, temperature change, and change in hyperspectral reflectance response.

3. The method of claim 2, wherein the one or more temporal measurements comprises at least the growth rate.

4. The method of claim 3, wherein the growth rate comprises rate of change of mushroom height, rate of change of cap diameter, rate of change of cap curvature, rate of change of cap misshapenness or ratios thereof.

5. The method of claim 4, wherein the growth rate comprises the rate of change of cap diameter, the rate of change of mushroom height, or both.

6. The method of claim 2, wherein the one or more temporal measurements comprises at least both of the growth rate and the temperature change.

7. The method of claim 2, wherein the one or more temporal measurements comprises at least the rate of change of temperature.

8. The method of claim 2, wherein the one or more temporal measurements comprises at least the change in hyperspectral reflectance response.

9. The method of claim 8, wherein the change in hyperspectral reflectance response comprises a change in intensity at a short-wave infrared (SWIR) wavelength.

10. The method of claim 9, wherein the wavelength has a value in a range of 1325-1500 nm or 1875-2000 nm.

11. The method of claim 9, wherein the wavelength has a value of about 1450 nm or about 1950 nm.

12. The method of claim 1, wherein the pre-determined ripeness functions for each of the temporal measurements are a single pre-determined ripeness threshold for all of the temporal measurements, the single pre-determined ripeness threshold defined in a common ripeness scale for any combination of temporal measurements.

13. The method of claim 12, wherein the single pre-determined ripeness threshold is an indicator of when the mushroom is ready to be harvested.

14. A method of harvesting a growing mushroom, the method comprising:
    determining ripeness of the growing mushroom by a method as defined in claim 13; and,
    picking the growing mushroom if the comparing of the temporal measurements for the one or more features to the pre-determined ripeness functions for each of the temporal measurements indicates that the growing mushroom is ready to be harvested.

15. The method according to claim 14, wherein a change in environmental conditions in which the mushroom is growing is factored into determining when the mushroom is picked.

16. The method of claim 1, wherein the measuring of one or more features of the growing mushroom further comprises obtaining one or more current measurements for the one or more features, wherein the one or more current measurements are analyzed to assist with the determining of the ripeness of the mushroom.

17. A system for determining ripeness of a growing mushroom, the system comprising:
    one or more imaging devices for obtaining a sequence of images of a growing mushroom over a period of time; and,
    a computer operatively connected to the one or more imaging devices, the computer configured to receive image data from the one or more imaging devices, the computer programmed to
    measure from the image data one or more features of the growing mushroom to obtain temporal measurements for the one or more features, the temporal measurements indicating rates at which the one or more features are changing, and
    compare the temporal measurements for the one or more features to pre-determined ripeness functions for each of the temporal measurements to determine the ripeness of the mushroom.

18. The system of claim 17, wherein the imaging devices comprise one or more cameras.

19. The system of claim 17, wherein the imaging devices comprise at least a 2-D visual light camera.

20. The system of claim 17, wherein the one or more temporal measurements comprises one or more of growth rate, color brightness change, temperature change, and change in hyperspectral reflectance response.

21. The system of claim 17, wherein the one or more temporal measurements comprises at least growth rate.

22. The system of claim 17, wherein the pre-determined ripeness functions for each of the temporal measurements are a single pre-determined ripeness threshold for all of the temporal measurements, the single pre-determined ripeness threshold defined in a common ripeness scale for any combination of temporal measurements, and wherein the single pre-determined ripeness threshold is an indicator of when the mushroom is ready to be harvested.

* * * * *